(12) United States Patent
Chung et al.

(10) Patent No.: US 7,544,327 B2
(45) Date of Patent: Jun. 9, 2009

(54) BIOSENSOR AND METHOD FOR BONE MINERAL DENSITY MEASUREMENT

(75) Inventors: Yung Ming Chung, Changhua County (TW); Yu Ching Liu, Taichung County (TW)

(73) Assignee: Industrial Technology Research Institute, Hsinchu (TW)

( * ) Notice: Subject to any disclaimer, the term of this patent is extended or adjusted under 35 U.S.C. 154(b) by 985 days.

(21) Appl. No.: 10/820,824

(22) Filed: Apr. 9, 2004

(65) Prior Publication Data

US 2005/0059875 A1 Mar. 17, 2005

(30) Foreign Application Priority Data

Aug. 27, 2003 (TW) .............................. 92123622 A

(51) Int. Cl.
*C12Q 1/68* (2006.01)
*G01N 33/573* (2006.01)
*G01N 19/10* (2006.01)
*G01N 21/00* (2006.01)
*A61B 5/05* (2006.01)
*A61K 9/20* (2006.01)
*A61K 39/395* (2006.01)

(52) U.S. Cl. ................... 422/82.05; 600/407; 435/6; 435/7.4; 424/464; 424/145.1; 73/23.2

(58) Field of Classification Search ............. 422/82.05; 600/407; 435/6, 7.4; 424/464, 145.1; 73/23.2
See application file for complete search history.

(56) References Cited

U.S. PATENT DOCUMENTS

| 6,248,544 | B1 * | 6/2001 | Halleen et al. ............... 435/7.4 |
| 6,289,717 | B1 * | 9/2001 | Thundat et al. ............... 73/23.2 |
| 7,217,428 | B2 * | 5/2007 | Tuszynski et al. ........... 424/464 |
| 2002/0137082 | A1 * | 9/2002 | Lewandrowski et al. ....... 435/6 |
| 2007/0134245 | A1 * | 6/2007 | Kostenuik et al. ......... 424/145.1 |

* cited by examiner

*Primary Examiner*—Jill Warden
*Assistant Examiner*—Lore Ramillano
(74) *Attorney, Agent, or Firm*—Bacon & Thomas, PLLC

(57) ABSTRACT

This invention is related a biosensor for bone mineral density measurement, comprising a stimulating source; a transducer having antibodies against TRAP 5a, TRAP 5b or total TRAP (i.e. TRAP 5a+TRAP 5b) immobilized thereon; a signal detecting unit; and a signal processing unit; wherein the TRAP refers to tartrate-resistant acid phosphatase (TRAP). The method for bone mineral density measurement disclosed in this invention is detecting the concentration or activity of TRAP, TRAP 5a and TRAP 5b in blood by using the biosensor described above. Accordingly, the method can monitor changes of the bone mineral density to prevent osteoporosis.

5 Claims, 2 Drawing Sheets

BIOSENSOR AND METHOD FOR BONE MINERAL DENSITY MEASUREMENT

BACKGROUND OF THE INVENTION

1. Field of the Invention

The present invention relates to a biosensor and method for bone mineral density measurement, which can monitor changes in bone mineral density (BMD) by detecting the content of tartrate-resistant acid phosphatase (TRAP) in blood.

2. Description of Related Art

Osteoporosis is one of the most common chronic illnesses among the elderly people. Statistics shows that osteoporosis hits approximately 20 million people and is the cause of about 1,300,000 fracture incidents in the United States each year. Treatment of fracture increases medical expenses to the tune of about US$14 billion a year. Japan is a geriatric society with a population of 120 million people, and about 5 million of which are afflicted with osteoporosis and potential patients may be as many as 10 million. Taiwan has a population of 20 million people. More than 30,000 people who suffer from fracture of femur each year could be attributed to osteoporosis, and 5% to 25% of those patients died of fracture-related complications.

Bone mineral density peaks in the age of 30 in both men and women and declines gradually thereafter. If no preventive action is taken, signs of osteoporosis will appear in the age of 40, particularly in women. What should be noted is that this disorder begins without any symptoms. For women over the age of 50 who are in menopause, the loss of bone mass accelerates. Related symptoms of osteoporosis begin to surface in patients over age 60 or are manifested directly in fracture.

Normal bone tissue carries on the process of formation and resorption continuously through the actions of osteoblasts and osteoclasts to maintain the balance of bone mineral density. But when osteoclasts become more active than osteoblasts, bone fracture, which is a bone resorption disorder, tends to occur. There are two kinds of bone resorption disorder: First, osteoporosis commonly presented in post-menopausal women, elderly people and people on steroid therapy; second, bone disorder caused by hyperparathyroidism. When osteoporosis-related fracture occurs, the bone mineral density in the patient is typically 60~70% or lower of that in normal people at their peak. At this time no effective and safe regimen is available to restore the bone mineral density. The condition of the patient can only be kept from deteriorating. Thus prevention of osteoporosis is very important.

Commonly used techniques for measuring bone mineral density include bone puncture, DEXA (dual energy X-ray absorptionmetry), and sonography. Bone puncture is an accurate but invasive procedure, which involves the extraction of bone mass from spine area. This procedure carries risk and is not well accepted by patients. DEXA is the main device used by the hospitals to measure bone mineral density (BMD). In DEXA, two low-dosage x-ray beams with differing energy levels are aimed at the patient's spine, hip or whole body. The computer calculates the content of BMD based on the fact that different bones absorb different energy levels. DEXA is also highly accurate. But the apparatus is bulky and expensive and emits radiation. The US FDA has approved a few products that use sonography to measure BMD. Such devices measure the BMD of peripheral bones, such as heel, shin bone and kneecap. But the BMD in spine or hip change faster than that in heel, shin bone or kneecap. Thus sonography is not as accurate or sensitive as DEXA in the determination of BMD. DEXA allows early detection of abnormal change in bone mass for its targets spine, hip or whole body. But sonography offers the advantages of low cost and radiation-free.

Tartrate-resistant acid phosphatase (TRAP) is an enzyme secreted by osteoclasts. Its activity or concentration has been shown to have relations with the rate of bone resorption and formation. Thus TRAP in blood is often used as an index of bone resorption and formation rate and applied in the monitoring of BMD. There are two forms of TRAP: TRAP 5a and TRAP 5b, of which TRAP 5b is a more meaningful index. The U.S. Pat. No. 6,248,544 discloses an immunoassay for measuring the level of TRAP and defines its activity by spectrophotometer to determine bone resorption and formation rate, and based on which to diagnose osteoporosis disorder or monitor the prognosis of osteoporosis treatment. However the immunoassay provided is time consuming that does not allow quick test.

In summary, there is a need to develop small-sized biosensor that allows quick testing and easy reading of BMD to facilitate the monitoring of bone mass change and prevention of osteoporosis.

SUMMARY OF THE INVENTION

In addressing the drawbacks of known bone mineral density detection technologies, the present invention provides a biosensor and method for measuring bone mineral density.

The method for measuring bone mineral density according to this invention utilizes a sensor comprised of a transducer to monitor the change in bone mineral density (BMD) through the measurement of a bone resorption/formation index—tartrate-resistant acid phosphatase (TRAP). First, immobilize antibodies against total TRAP, TRAP 5a or TRAP 5b on the surface of said transducer and then let the specimen react with said antibodies on the surface of said transducer, wherein the total TRAP, TRAP 5a or TRAP 5b contained in the specimen are bound with said antibodies (antigen-antibody specific binding reaction). After the antigen-antibody binding reaction, the transducer surface will undergo changes. These surfaced changes will induce the variations of crystal, audio oscillation frequency or deflection of the transducer, which may be detected with proper instrumentation. From the detection results, the amount of enzyme bound on the transducer surface may be computed, and based on which, the BMD in the specimen is determined.

An objective of the present invention is to provide a biosensor for bone mineral density measurement, comprising a stimulating source for energy supply; a transducer with antibodies against TRAP 5a, TRAP 5b or total TRAP (i.e. TRAP 5a+TRAP 5b) immobilized thereon; a signal detecting unit for detecting the change in signals from said transducer; and a signal processing unit for retrieving and analyzing said signals.

Said transducer includes cantilever beam, surface acoustic wave (SAW) device, and quartz crystal microbalance (QCM) sensor. When the transducer is a cantilever beam, its stimulating source is light source, preferably having wavelength ranging from 635 nm to 850 nm, which can be provided by using laser or laser dioxide. When the transducer is a SAW or QCM, its simulating source is voltage or current source, which can be provided by using power supply.

In the first embodiment of the biosensor according to this invention, the transducer is a cantilever beam, which is made of special material (e.g. silicon or silicon nitride) and oscillates freely with the structure of a flexible springboard. When the substance is very close to or in contact with the surface of cantilever beam, the interacting forces between the substance and the cantilever, such as repulsion, attraction, adhesion, friction and magnetic forces, will cause the deflection of the cantilever beam. The percentage of deflection may be detected through various instruments, for example, but not limited to, photoelectric detector can be used to compare the difference of reflected light intensity in different quadrants when aiming laser at the back surface of the cantilever beam. While the relationship between the deflection and the mass of substance is obtained, the amount of deflection is then converted to the mass of substance on cantilever beam.

Besides measuring the deflection of cantilever beam, the amount (concentration) or activity of biomolecules adhered to the surface of cantilever beam may also be determined by measuring the shift in its resonance frequency. This is achieved by applying light pressure or electric voltage, or using other physical means to cause oscillation of the cantilever beam and then using photoelectric device to record its resonance frequency, and from which to obtain the relationship between the shift in resonance frequency and the mass of the substance adhered to the cantilever beam.

The aforesaid cantilever beam can be in any form, for example, but not limited to, triangle, rectangle, or array. Said cantilever beam is preferably made of, but not limited to, silicon, silicon nitride, poly-silicon or polymer. The surface material of said cantilever beam is preferably, but not limited to, gold, platinum or silicon.

In the second embodiment of the biosensor according to this invention, the transducer is a surface acoustic wave (SAW) device, which works by the principle described below: intermittently arranged metallic electrodes in the shape of a railing are fabricated onto the surface of a piezoelectric substrate (e.g. quartz, $LiNbO_3$ or $LiTaO_3$); such structure is also called interdigital transducer (IDT). The purpose of the transducer is convert the electronic signals received at input into surface acoustic signals, which are transmitted through the piezoelectric substrate to the output where the acoustic signals are converted back to electronic signals. After the IDT surface is adhered with a substance, the change of its acoustic wave signals and oscillation frequency is proportionally related to change to the mass of adhered substance. Thus by detecting the change in acoustic wave signals and oscillation frequency, the mass of adhered substance may be computed. In practical operation, biomolecules (e.g. antibodies) are immobilized on SAW surface. When such biomolecules react with the specimen, the biomolecules in the specimen (e.g. antigens) will bind with the biomolecules on SAW surface (e.g. antibodies), causing change to the surface acoustic wave on SAW. By detecting the audio oscillation frequency produced by change of acoustic wave, the mass of substance adhered to SAW surface may be computed, and from which, the weight of substance to be tested in the specimen may be obtained.

In the third embodiment of the biosensor according to this invention, the transducer is a quartz crystal microbalance (QCM), which works by the principle described below: two metallic electrodes (e.g. gold, silver, aluminum or nickel) are disposed on each side of piezoelectric substrate surface (e.g. quartz substrate) where the electrodes introduce an oscillating electric field longitudinal to the substrate surface, which forces the crystal lattice inside the piezoelectric substrate to produce mechanical oscillation similar to standing waves, through which a constant frequency is generated. The most important factor in changing the oscillation frequency of crystal is the change of electrode mass. Thus the mass of substance adhered on the electrode may be computed by measuring the change of crystal's oscillation frequency. In practical operation, biomolecules (e.g. antibodies) are immobilized on QCM surface. When such biomolecules react with the specimen, the biomolecules in the specimen (e.g. antigens) will bind with the biomolecules on QCM surface (e.g. antibodies), causing change to the oscillation frequency of QCM. By detecting the change of crystal oscillation frequency, the mass of substance adhered to QCM surface may be computed, and from which, the weight of substance to be tested in the specimen may be obtained.

The biomolecules immobilized on said transducer are preferably antibodies against total TRAP or TRAP 5b. Said antibodies against total TRAP, TRAP 5a or TRAP 5b are immobilized on transducer surface by suitable compound and undergo specific binding with TRAP, TRAP 5a or TRAP 5b in the specimen to detect the change in bone mineral density Another objective of the present invention is to provide a biosensor for bone mineral density measurement, comprising a stimulating source; a substrate having at least one cantilever beam disposed thereon, wherein the surface of said cantilever beam is immobilized with antibodies against TRAP 5a, TRAP 5b or total TRAP (i.e. TRAP 5a+TRAP 5b); a signal detecting unit for detecting change of signals from said cantilever beam; and a signal processing unit for retrieving and analyzing said signals.

According to the present invention, said signal detecting unit comprises a position sensitive detector (PSD), used to detect the position deflection or shift in resonance frequency of cantilever beam resulting from change of mass, wherein the signals of deflection or resource frequency shift can be further amplified optically. A further objective of the present invention is to provide a method for measuring bone mineral density, comprising the steps of: obtaining a test specimen containing TRAP, TRAP 5a or TRAP 5b; letting said specimen react with transducer immobilized with antibodies against TRAP 5a, TRAP 5b or total TRAP (i.e. TRAP 5a+TRAP 5b); detecting the change of transducer signals; analyzing said signals; computing the concentration or activity of TRAP, TRAP 5a or TRAP 5b in the specimen based on the change of signals; and determining the change in bone mineral density based on the concentration or activity of TRAP, TRAP 5a or TRAP 5b obtained thereof.

In comparison with prior art (e.g. DEXA or sonography), the biosensor and method for bone mineral density measurement provided in the present invention offer the advantages of radiation-free, high sensitivity, small size, low price, quick testing, and easy reading, and have great potential for applications in the health care market.

DETAILED DESCRIPTION OF THE DRAWINGS

Figure 1:
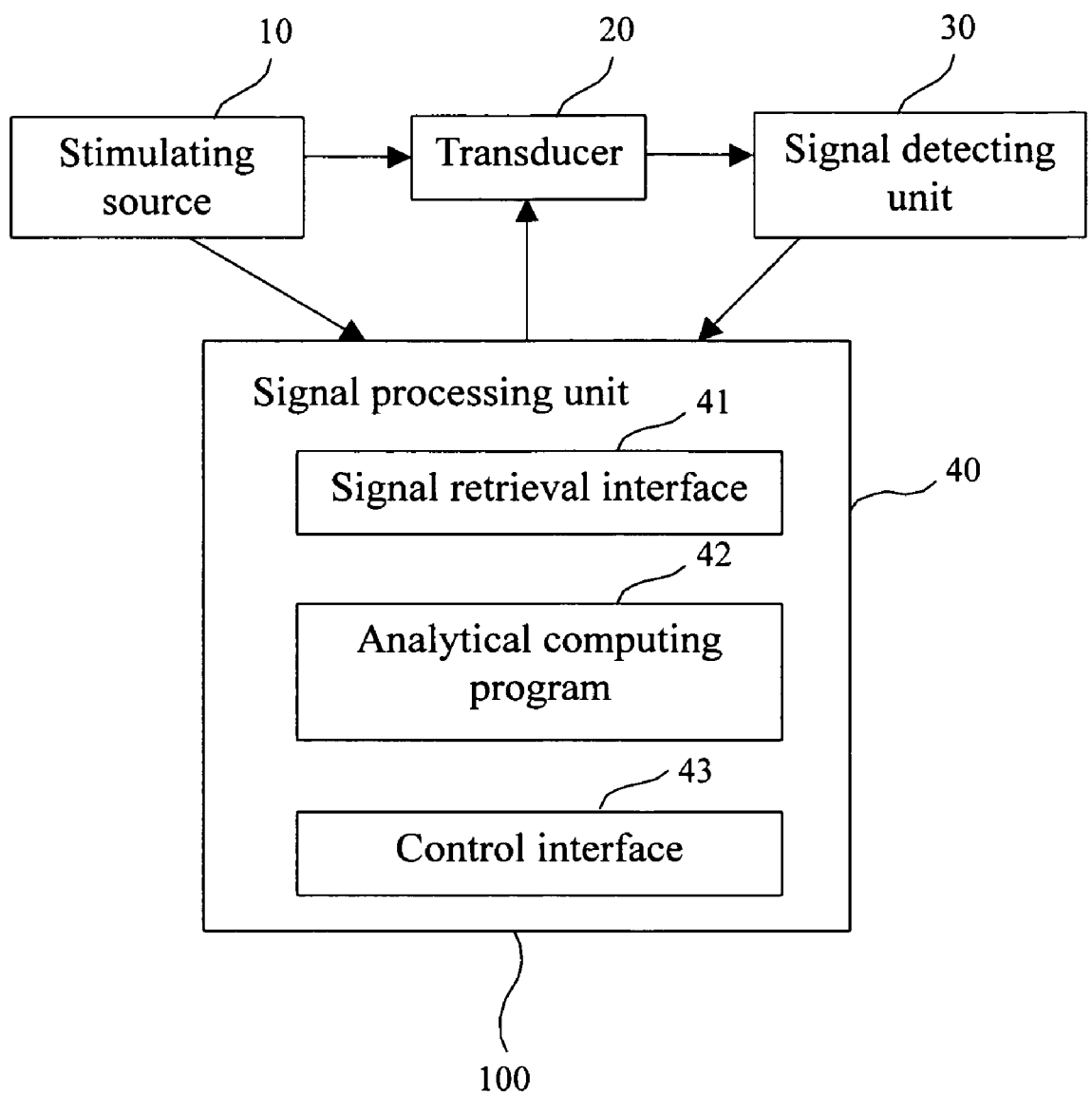
FIG. 1 shows the schematic diagram of biosensor for bone mineral density measurement according to the present invention.

The biosensor for bone mineral density measurement 100 of the present invention as shown in FIG. 1 comprises: a stimulating source 10, a transducer 20 having immobilized antibodies against TRAP 5a, TRAP 5b or total TRAP (i.e. TRAP 5a+TRAP 5b) thereon; a signal detecting unit 30 for detecting the change of signals from transducer 20; and a signal processing unit 40 for retrieving and analyzing said signals.

Said signal detecting unit 30 can be used to detect the change of transducer signals due to change of mass and process/transmit said signals through built-in circuit Said signal processing unit 40 comprises signal retrieval interface 41 (e.g. RS232, USB, DIO or DAQ), analytical computing program 42, and control interface 43 for controlling said stimulating source 10 and transducer 20.

Said transducer 20 can be in the form of cantilever beam, surface acoustic wave device or quartz crystal microbalance. When transducer 20 is cantilever beam, its stimulating source 10 is light source (e.g. laser or laser diode), preferably having wavelength of 635-850 nm; when transducer 20 is surface acoustic wave device or quartz crystal microbalance sensor, its stimulating source 10 is voltage or current source (e.g. power supply).

Figure 2:
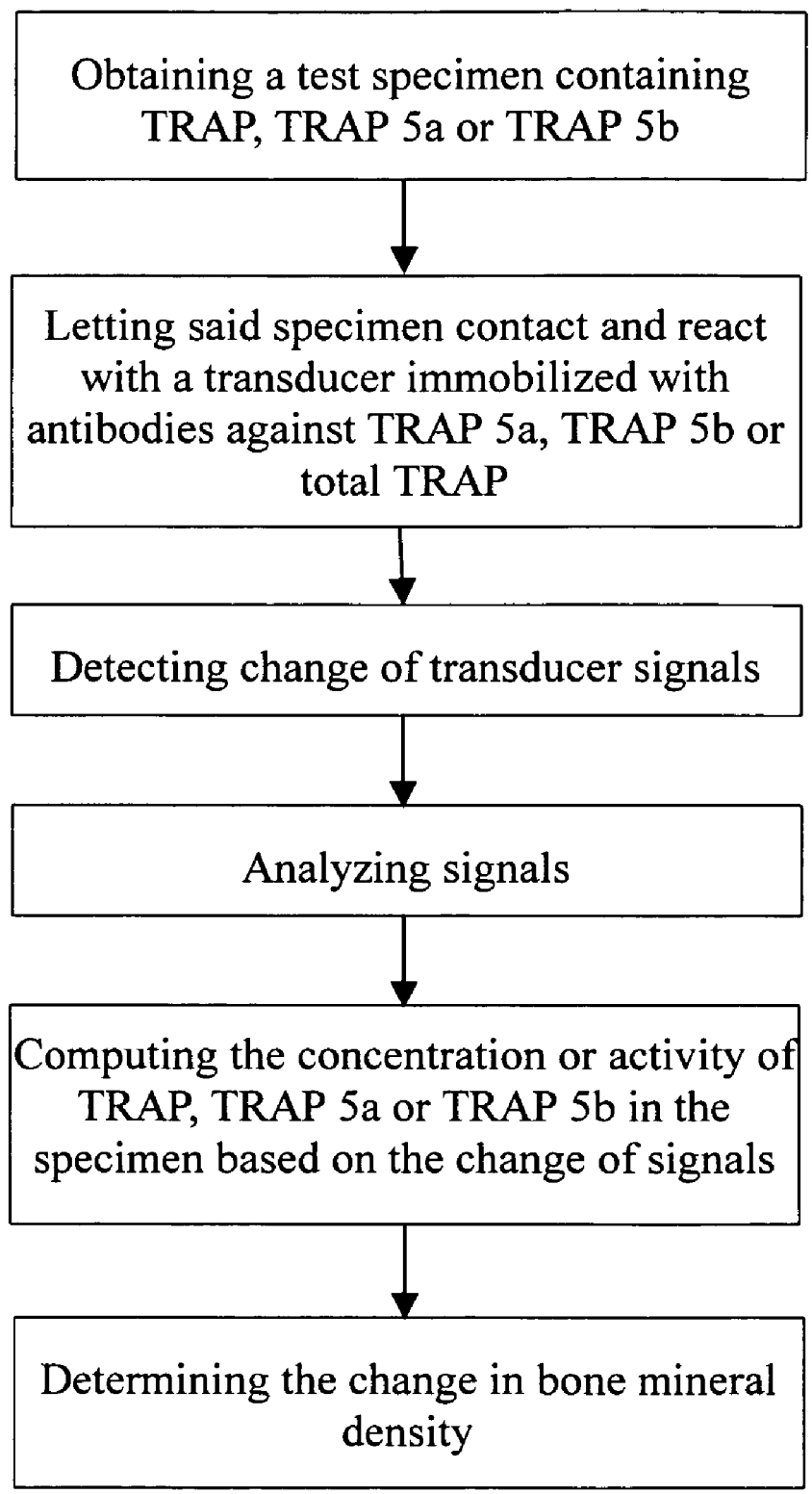
FIG. 2 shows the flow chart of the method for bone mineral density measurement according to the present invention.

The method for measuring bone mineral density of the present invention as shown FIG. 2 comprises the steps of: obtaining a test specimen containing TRAP, TRAP 5a or TRAP 5b, wherein said specimen may be blood or serum; letting said specimen contact and react with transducer immobilized with antibodies against TRAP 5a, TRAP 5b or total TRAP (i.e. TRAP 5a+TRAP 5b) so that such antibodies undergo antigen-antibody binding reaction with TRAP 5a, TRAP 5b or total TRAP in the specimen; if the antibodies on the surface of the transducer bind with the enzymes in the specimen, change of transducer signals will occur. Because the change of transducer signal is proportionally related to the change of its weight, the concentration or activity of TRAP, TRAP 5a or TRAP 5b in the specimen may be computed by detecting the change of transducer signals and analyzing and computing such change. Finally, change in bone mineral density may be determined based on the concentration or activity level of TRAP, TRAP 5a or TRAP 5b measured. For example, when the concentration or activity of the aforesaid enzyme increases, it means the number of osteoclast increases, which might lead to osteoporosis or fracture.

The advantages of the present invention are further depicted with the illustration of embodiments and examples, but the descriptions made in the examples should not be construed as a limitation on the actual application of the present invention.

EMBODIMENT 1

In this embodiment, the biosensor for bone mineral density measurement uses a highly sensitive mass-sensing cantilever beam (sensitivity up to $1 \times 10^{12}$ gram) as transducer, which is made of silicon in array configuration, and uses laser diode having wavelength of 635~850 nm as stimulating source. The immobilization of enzymes on the surface of cantilever beam may be achieved using any of the methods related to in literature, such as self-assembled monolayer, polymer coating and biomolecular modification. For example, first modify the surface of cantilever surface with gold and let the antibodies (e.g. antibodies against total TRAP or TRAP 5b) react with a compound having thiol functional group (e.g. cysteamine, PEI or sulfo-LC-SPDP) to form thiol-modified antibodies; hence said thiol-modified antibodies can be immobilized on the gold-covering surface of cantilever beam through self-assembly of thiol-modified antibodies and gold. [Ultramicroscopy 91, p. 29-36, 2002].

For measurement, drop the blood sample on the surface of cantilever beam. When the TRAP and/or TRAP 5b in blood binds with antibodies against total TRAP and/or TRAP 5b immobilized on cantilever surface, the added weight will cause deflection in position or shift in resonance frequency of cantilever beam. After optically magnifying the signals, use position sensitive detector to detect the deflection and send the signals to signal processing unit where the deflection information is retrieved by signal retrieval interface (DAQ) and sent to computing program for processing to obtain the amount of TRAP and/or TRAP 5b in the blood. Based on amount of TRAP and/or TRAP 5b, change in bone mineral density may be determined.

EMBODIMENT 2

In this example, the biosensor for bone mineral density measurement uses the surface acoustic wave (SAW) device as transducer and power supply that supplies voltage or current as stimulating source. The SAW is made of quartz piezoelectric substrate fabricated with intermittently arranged metallic electrodes in the shape of a railing (i.e. interdigital transducer). Subsequently, use a compound (e.g. cysteamine, PEI or sulfo-LC-SPDP) to immobilize antibodies against total TRAP and TRAP 5b on the surface of piezoelectric substrate. The immobilization method is the same as that described in Embodiment 1.

For measurement, drop the blood sample on the surface of SAW substrate. When the TRAP and/or TRAP 5b in blood binds with antibodies against total TRAP and/or TRAP 5b immobilized on SAW substrate surface, the added weight will cause change of acoustic signals, which are transmitted by IDT and finally to the signal processing unit for analysis and computation. Because the change of audio oscillation frequency is proportional to the mass change of the adhered substance, the concentration of TRAP and/or TRAP 5b in blood may be obtained, and based on which, the change in bone mineral density is determined.

EMBODIMENT 3

In this embodiment, the biosensor for bone mineral density measurement uses quartz crystal microbalance (QCM) as transducer and power supply that supplies voltage or current as stimulating source. The working theory of QCM is similar to that of SAW. The QCM has a quartz piezoelectric substrate, which is fabricated with two metallic electrodes (e.g. gold, silver, aluminum or nickel) on each side. Subsequently, use a compound (e.g. cysteamine, PEI or sulfo-LC-SPDP) to immobilize antibodies against total TRAP and TRAP 5b on the surface of piezoelectric substrate. The immobilization method is the same as that described in Embodiment 1.

For measurement, drop the blood sample on the surface of QCM substrate. When the TRAP and/or TRAP 5b in blood binds with antibodies against total TRAP and/or TRAP 5b immobilized on QCM substrate surface, the added weight will produce change in electrode mass, thereby causing change in oscillation frequency of the crystal. The change signals are transmitted via the electrodes to signal processing unit for analysis and computation. Because the change of crystal oscillation frequency is proportional to the mass change of the adhered substance, the concentration of TRAP and/or TRAP 5b in the blood may be obtained, and based on which, the change in bone mineral density is determined.

EXAMPLE 1

Enzyme Immobilization

The immobilization of enzymes on the surface of cantilever beam may be achieved by using any of the methods related to in literature, such as self-assembled monolayer, polymer coating and biomolecular modification.

The detail examples of enzyme immobilization are described below, but other processes for enzyme immobilization are also be utilized.

A. Self-Assembled Monolayer(SAM)

First, immerse the cantilever beam in 1.2N NaOH solution for 2 hours to remove pollutants on the surface of cantilever beam and then wash with DI water, followed by immersing in 1M HCl for 5 minutes and washing in sequencewith DI water for 5 minutes, concentration HCl for 2 minutes and DI water for 5 minutes. The cantilever beam was then immersed in 20 mM Cystamine solution over 24 hr and washed with DI water for 5 min. After reacting with 2.5% Gultaaldehyde for 3 hr, immobilize TRAP antibodies on gold surface of said cantilever beam over night. Finally, immerse the cantilever beam in 5% SDS solution in ultrasonic for 5 min and wash 3 times with DI water to remove unbound antibodies, then a cantilever beam modified with antibodies is obtained.

B. Biomolecular Modification

The cantilever beam was immersed in 1.2N NaOH solution for 2 hours to remove pollutants on the surface of cantilever beam and washed with DI water, then immersed in 1.2N HCl for 5 minutes, washed with DI water and dried in oven.

0.5 μg/μL Anti-antigens and 10 μL 20 mM Sulfosuccinimidyl 6-[3-(2-pyridyldithio)propionamido]hexanoate(Sulfo-LC-SPDP) was add into a microcentrifuge tube and mixed completely to react for 90 min. 5 μL 20 mM dithiothreitol (DTT) was subsequently added to the above solution and reacted for 30 min. The reaction solution was sprayed on the gold surface of cantilever beam for immobilization. Reaction was continued at 4° C. for 4 hours. After the reaction, the cantilever beam was immersed in 5% SDS solution in ultrasonic for 5 min and washed 3 times with DI water to remove unbound antibodies. Finally, a cantilever beam modified with antibodies is obtained.

EXAMPLE 2

The cantilever beam modified with antibodies as described in example 1 was immersed in 0.5 μg/μL TRAP for 2 hours. When the TRAP bound with TRAP antibodies immobilized on cantilever surface, the added weight would cause shift in resonance frequency of cantilever beam. In this example, the resonance frequency of cantilever beam was measured by Auto tune of Atomic Force Microscope. The resonance frequency of cantilever beam as unmodified, modified with TRAP antibodies and reacted with antigens were measured. The parameter of start frequency is 0 kHz, end frequency is 40 kHz and drive amplitude is 0.5V. The test results are shown in table 1, wherein the resonance frequency of cantilever beam modified with TRAP antibodies was slower than that of unmodified cantilever beam and that of cantilever beam reacted with TRAP antigens was slower than that of cantilever beam modified with TRAP antibodies. Analyze the relationship between the resonance frequency shift and the mass of biomolecular, then the mass of TRAP antigens could be figured out.

EXAMPLE 3

The cantilever beam modified with antibodies as described in example 1 was immersed in 0.5 μg/μL TRAP for 2 hours. The attachment of antibodies and antigens changed the surface stress on cantilever beam, causing the position deflection of cantilever beam. In this example, the position deflection of cantilever beam was measured by optic detection plate. The position deflection of cantilever beam modified with TRAP antibodies and reacted with antigens was measured, wherein the position of cantilever beam modified with TRAP antibodies was set as reference. The test results are shown in table 2. Analyze the relationship between the position deflection and the mass of biomolecular, then the mass of TRAP antigens can be figured out.

TABLE 2

| REF (m) | TEST (m) | Difference (m) | DISP (m) | Surface Stress (N/m) |
|---|---|---|---|---|
| 1.5000E−04 | 1.10000E−04 | 4.0000E−05 | 7.0000E−08 | 1.29524E−01 |

REF: reference position of the cantilever beam
TEST: the position of the cantilever beam reacted with TRAP antigens
Difference: REF − TEST
DISP: the position deflection of cantilever beam
Surface Stress: the surface stress that caused by the amount of the TRAP According to the above description, the biosensor and method for bone mineral density measurement provided in the present invention may utilize various transducers and offer high detection sensitivity. In comparison with known equipments and technologies for measuring bone mineral density, the present invention offers the advantages of small size, low price, quick testing and easy reading.

The preferred embodiment of the present invention as disclosed above is not meant to limit this invention. All modifications and alterations made by those familiar with the skill without departing from the spirits of the invention and appended claims shall remain within the protected scope and claims of the invention.

What is claimed is:

1. A biosensor for measuring bone mineral density, comprising: a stimulating source; a transducer having at least one cantilever beam disposed thereon, wherein the surface of said cantilever beam is immobilized with antibodies against TRAP 5a, TRAP 5b or total TRAP; a signal detecting unit for detecting signal changes from said transducer; and a signal processing unit for retrieving and analyzing said signals.

2. The biosensor according to claim 1, wherein said stimulating source is laser or laser diode.

3. The biosensor according to claim 1, wherein said signal detecting unit comprises a position sensitive detector for

TABLE 1

| | Blank (Hz) | Frequency 1 (Hz) | Frequency 2 (Hz) | Mass 1 (g) | Mass 2 (g) | Mass of TRAP (g) |
|---|---|---|---|---|---|---|
| TRAP 5U | 2.49796E+04 | 2.49370E+04 | 2.49334E+04 | 4.16867E−14 | 4.52193E−14 | 3.53261E−15 |
| TRAP 10U | 2.78305e+04 | 2.77245E+04 | 2.77227E+04 | 7.52422E−14 | 7.65274E−14 | 1.28516E−15 |

Blank: unmodified cantilever beam
Frequency 1: cantilever beam modified with TRAP antibodies
Frequency 2: TRAP antibodies immobilized on cantilever beam reacted with TRAP antigens
Mass 1: mass of TRAP antibodies immobilized on the surface of cantilever beam
Mass 2: total mass of TRAP antibodies and antigens on the surface of cantilever beam detecting deflection or shift in resonance frequency of said transducer caused by mass change.

4. The biosensor according to claim 3, wherein the signals of deflection or resonance frequency shift can be further amplified optically.

5. The biosensor according to claim 1, wherein biomolecules immobilized on said transducer are antibodies against total TRAP or TRAP 5b.

* * * * *